United States Patent [19]

Bonrath et al.

[11] Patent Number: 5,502,212

[45] Date of Patent: Mar. 26, 1996

[54] PROCESS FOR THE MANUFACTURE OF 5-CYANO-4-LOWER ALKYL-OXAZOLES

[75] Inventors: Werner Bonrath, Freiburg; Reinhard Karge, Staufen, both of Germany; Horst Pauling, Bottmingen, Switzerland

[73] Assignee: Hoffmann-La Roche Inc., Nutley, N.J.

[21] Appl. No.: 197,426

[22] Filed: Feb. 16, 1994

[30] Foreign Application Priority Data

Feb. 25, 1993 [CH] Switzerland ................ 578/93

[51] Int. Cl.⁶ .................................... C07D 263/30
[52] U.S. Cl. ............................................ 548/236
[58] Field of Search ................................ 548/236

[56] References Cited

U.S. PATENT DOCUMENTS

| | | | |
|---|---|---|---|
| 3,222,374 | 12/1965 | Chase | 548/236 |
| 4,026,901 | 5/1977 | Coffen | 548/236 |
| 4,093,654 | 6/1978 | Coffen . | |
| 4,255,584 | 3/1981 | Hoffmann-Paquotte | 548/236 |
| 4,772,718 | 9/1988 | Nosberger | 548/236 |
| 5,214,162 | 5/1993 | Nosberger | 548/236 |

FOREIGN PATENT DOCUMENTS

| | | |
|---|---|---|
| 10697 | 5/1980 | European Pat. Off. . |
| 492233 | 7/1992 | European Pat. Off. . |

OTHER PUBLICATIONS

Olah, et al., Synthesis, 78: pp. 657–658 (1980).

*Primary Examiner*—Donald G. Daus
*Attorney, Agent, or Firm*—George M. Gould; William H. Epstein; Bruce A. Pokras

[57] ABSTRACT

A process for the manufacture of 5-cyano-4-lower alkyl-oxazoles is described in which a 5-carbamoyl-4-lower alkyl-oxazole is dehydrated in an organic solvent under mild conditions with cyanuric chloride and an N,N-disubstituted-formamide.

6 Claims, No Drawings

PROCESS FOR THE MANUFACTURE OF 5-CYANO-4-LOWER ALKYL-OXAZOLES

BACKGROUND OF THE INVENTION

The present invention is concerned with a novel process for the manufacture of 5-cyano-4-lower alkyl-oxazoles. These oxazoles form an important group of substances. For example, 5-cyano-4-methyl-oxazole is an important intermediate in the synthesis of pyridoxine (vitamin $B_6$).

A number of processes for the manufacture of 5-cyano-4-methyl-oxazole by dehydrating 5-carbamoyl-4-methyl-oxazole have already been described. This dehydration takes place, for example, in the presence of phosphorus pentoxide. The disadvantage of this process is, however, the low product yield, which is attributed to the carbonization which occurs very readily in this reaction.

An improvement in this process comprises reacting 5-carbamoyl-4-methyl-oxazole with phosphorus pentoxide in the presence of quinoline as a solvent [U.S. Pat. No. 3,222,374]. This process is also associated with disadvantages which arise from the toxicity of the quinoline, its unpleasant odor and its thermal instability. Moreover, quinoline is a relatively expensive solvent. Furthermore, the regeneration of the quinoline, the use of stoichiometric amounts of phosphorus pentoxide, the working-up of the phosphorus pentoxide by-products and their disposal according to environmental regulations, give rise to problems.

Another known process for the manufacture of 5-cyano-4-methyl-oxazole comprises reacting 5-carbamoyl-4-methyl-oxazole with a lower alkanecarboxylic acid anhydride and subjecting the reaction mixture, or the 4-methyl-5-(N-lower alkanoyl-carbonyl)-oxazole isolated therefrom, to a pyrolysis [European Patent Application EP 0 010 607]. The final pyrolytic step has, however, certain disadvantages; in particular, corrosion problems occur with the materials from which the reactor is constructed and by-products which are difficult to recyclize from.

A further process [U.S. Pat. No. 4,026,902] comprises catalytically dehydrating 5-carbamoyl-4-methyl-oxazole to 5-cyano-4-methyl-oxazole while heating in the presence of phosphorus pentoxide on a solid carrier. Disadvantages in this process are the handling of 5-carbamoyl-4-methyl-oxazole, especially the sublimation which is uppermost and therewith the solid dosing of the difficultly volatile starting material.

Furthermore, the one-stage conversion of 5-carboxylic acid ethyl ester-4-methyl-oxazole into 5-cyano-4-methyl-oxazole is described in U.S. Pat. No. 4,772,718. In this process, the corresponding oxazole ester is converted into 5-cyano-4-methyl-oxazole in the presence of ammonia and a zirconium oxide or hafnium oxide catalyst in the gas phase. Here, however, the use of a relatively expensive catalyst and, in order to achieve an optimal reaction course, the maintenance of very narrow reaction conditions, are disadvantageous.

Finally, the gas phase dehydration of 5-carbamoyl-4-methyl-oxazole to 5-cyano-4-methyl-oxazole described in European Patent Application EP 0 492 233 has the disadvantage of a reaction temperature of 400° C.–500° C. and must be carried out at a pressure of 50 to about 300 kPa.

Olah et al., *Synthesis*, 1980:657–658, (August 1980), describe a general method of preparing nitriles from amides by dehydration. The procedure describes adding cyanuric chloride to a solution of the amide in dimethylformamide. The method described by Olah is not practicable for the object of the present invention because of the exothermic reaction (Handbook of Reactive Chemical Hazards, fourth edition, Butterworth 1990, page 331–333). For Olah et al. the exothermic reaction presented no problem as they were only interested in preparing very small amounts of nitrile. Using cyanuric chloride and 5-carbamoyl-4-methyl-oxazole without dimethylformamide led to very low yields (≈1%) of the corresponding nitrile.

SUMMARY OF THE INVENTION

The object of the present invention is to provide a process for the manufacture of 5-cyano-4-lower alkyl-oxazoles which does not have the disadvantages of the previously known procedures, and in accordance with which 5-cyano-4-lower alkyl-oxazoles can be obtained in a short reaction time under mild reaction conditions in high yield.

In accordance with the invention, it has been surprisingly found that carrying out the dehydration of a 5-carbamoyl-4-lower alkyl-oxazole in an organic solvent led to nearly quantitative yields of 5-cyano-4-lower alkyl-oxazoles. Thus, the process of the invention comprises carrying out the dehydration of a 5-carbamoyl-4-lower alkyl-oxazole by dehydrating, in an organic solvent, said 5-carbamoyl-4-lower alkyl-oxazole with cyanuric chloride and an N,N-disubstituted formamide.

DETAILED DESCRIPTION OF THE INVENTION

The term "lower alkyl" signifies in the scope of the present invention straight-chain or branched alkyl groups with 1 to 6 carbon atoms such as, e.g., methyl, ethyl, propyl, iso-propyl, butyl, iso-butyl, tert.butyl, pentyl, hexyl and the like. Straight-chain alkyl groups are preferred, with methyl and ethyl being especially preferred.

In accordance with the invention, it has been surprisingly found that carrying out the dehydration of a 5-carbamoyl-4-lower alkyl-oxazole in an organic solvent, using cyanuric chloride and a N,N-disubstituted formamide, led to nearly quantitative yields of the corresponding 5-cyano-4-lower alkyl-oxazoles.

The N,N-disubstituted formamide used in accordance with the invention is not critical. Any conventional N,N-disubstituted formamide can be utilized in accordance with the invention. The use of an N,N-disubstituted formamide for the dehydration of an amide is known in the art. [Olah et al., supra.]. Substituents on the N,N-disubstituted formamide are preferably lower alkyl. N,N-disubstituted formamides in the scope of the present invention may be open-chain formamides. Preferred are N,N-dimethylformamide ("DMF"), N,N-diethylformamide, and N,N-di-n-propylformamide. Also in the scope of the present invention are formamides in which the substituents are part of a ring. Preferred formamides in which the substituents are part of a ring are N-formylmorpholine, N-formylpyrrolidine, and N-formylpiperidine. DMF is the especially preferred formamide.

In accordance with the invention, the dehydration of a 5-carbamoyl-4-lower alkyl-oxazole using cyanuric chloride and an N,N-disubstituted formamide is carried out in an organic solvent. Any organic solvent may be used in accordance with the invention. Since the reaction mixture will be neutralized and washed with aqueous media, the solvent should not be soluble in water. The preferred solvents are methyl tertiary butyl ether, ethyl tertiary butyl ether, tertiary amyl methyl ether, DMF, N,N-diethylformamide, N,N-di-n- propylformamide, N-formylmorpholine, N-formylpyrrolidine, and N-formylpiperidine. Although hexane may be used. Although DMF may be used as both the polar aprotic organic cosolvent and as the N,N-disubstituted formamide in the reaction of the invention, in such a case, the reaction that occurs is highly exothermic. Methyl tertiary butyl ether is the especially preferred polar aprotic organic solvent for use in carrying out the reaction in accordance with the invention.

The dehydration reaction in accordance with the invention is carried out by mixing together the 5-carbamoyl-4-lower alkyl-oxazole, the N,N-disubstituted formamide, cyanuric chloride, and the organic solvent. The sequence in which the reactants are combined is not critical, except that to prevent an overly exothermic reaction the DMF and the cyanuric chloride should not be combined in the absence of the organic solvent. The sequence described below is preferred, wherein the organic solvent and the cyanuric chloride are added together as a cyanuric chloride solution. Optionally, the oxazole may be suspended in the organic solvent, in addition to or in replacement of the solvent which was used to dissolve the cyanuric chloride.

The temperature and pressure at which the dehydration reaction of the invention is carried out is not critical. The dehydration can be conveniently carried out in a temperature range of about 0° C. to about 50° C., preferably at about room temperature. The preferred pressure is atmospheric pressure.

In the preferred embodiment of the invention, the 5-carbamoyl-4-lower alkyl-oxazole is suspended in the pure N,N-disubstituted formamide. The cyanuric chloride in the organic solvent is then added to the above-described mixture.

The molar ratio of 5-carbamoyl-4-lower alkyl-oxazole:cyanuric chloride is not critical. The reaction is preferably carried out at a molar ratio of about 3:1 to 3:10. It is especially preferred that the reaction be carried out at a 5-carbamoyl-4-lower alkyl-oxazole:cyanuric chloride molar ratio of about 3:1 to 1:1, particularly at a 5-carbamoyl-4-lower alkyl-oxazole:cyanuric chloride molar ratio of about 2:1.

The molar ratio of N,N-disubstituted formamide to cyanuric chloride in the reaction of the invention is not critical. The molar ratio of N,N-disubstituted formamide to cyanuric chloride is preferably at least 3:1, although a larger excess of the formamide is especially preferred.

The amount of organic solvent can vary over a wide range. In carrying out the reaction of the invention, the organic solvent should be present in an amount which will result in a solution in the solvent of the 5-carbamoyl-4-lower alkyl-oxazole and the cyanuric chloride to be reacted. The preferred ratio of the total weight of the oxazole and cyanuric chloride (in grams) to the volume of the solvent (in milliliters) is from about 1:1 to about 1:25. This is based upon the use in the Example, infra, of about 40 g (total) of the oxazole and cyanufic chloride, and the potential use in accordance with the Example of from about 50 ml to about 1000 ml of the solvent. In this manner, the ratio disclosed in the Example is about 1:5. It is especially preferred that the ratio be at least about 1:2.

After neutralization of the reaction mixture, the working-up of the crude product to the 5-cyano-4-lower alkyl-oxazole may be carried out by any conventional means, e.g., by extraction with solvents such as methyl tertiary butyl ether, diethyl ether, diisopropyl ether, tertiary amyl methyl ether, ethyl acetate, methyl acetate, isobutyl methyl ketone, pentane, heptane, dichloromethane and the like. Extraction with methyl tertiary butyl ether is especially preferred. Any conventional bases may be used for the neutralization of the reaction mixture. Inorganic bases such as NaOH, $Na_2CO_3$ and the like as well as organic bases such as, e.g., amines, are suitable for the neutralization. Ethylamine, diethylamine, triethylamine, pyridine and the like are suitable amines.

An almost quantitative conversion of a 5-carbamoyl-4-lower alkyl-oxazole into a 5-cyano-4-lower alkyl-oxazole can be achieved by means of the process in accordance with the invention.

The following Example for the manufacture of 5-cyano-4-methyl-oxazole illustrates an especially advantageous embodiment of the process in accordance with the invention and is not intended in any way to be a limitation.

EXAMPLE 22.88 g (198 mmol) of 5-carbamoyl-4-methyl-oxazole are suspended in 100 ml of N,N-dimethylformamide at room temperature and treated within 15 minutes with 18.31 g (99.3mmol) of cyanuric chloride in 250 ml of methyl tertiary butyl ether. The mixture is stirred at room temperature for one hour, whereby the initially yellow suspension becomes orange. Subsequently, it is neutralized with 50 ml of saturated aqueous $Na_2CO_3$ solution, the phases are separated, the aqueous phase is extracted twice with 150 ml of methyl tertiary butyl ether each time and the combined organic phases are washed with 250 ml of dist. water, dried over $Na_2SO_4$, filtered and concentrated on a rotary evaporator. An orange, liquid crude product remains. The yield of 5-cyano-4-methyl-oxazole is 99.4% of theory (determined by gas chromatography).

We claim:

1. A process for the manufacture of a 5-cyano-4-lower alkyl-oxazole, which comprises reacting, in a polar, aprotic organic solvent selected from the group consisting of methyl tertiary butyl ether, ethyl tertiary butyl ether and tertiary amyl methyl ether, a 5-carbamoyl-4-lower alkyl-oxazole with an N,N-disubstituted formamide and cyanuric chloride to dehydrate said 5-carbamoyl-4-lower alkyl-oxazole and thereby produce said 5-cyano-4-lower alkyl-oxazole, wherein the ratio of the total weight of the 5-cyano-4-lower alkyl-oxazole and the cyanuric chloride, in grams, to the volume of the solvent, in milliliters, is from about 1:2 to about 1:25.

2. The process of claim 1, wherein the dehydration is carried out at a temperature of from about 0° C. to about 50° C.

3. The process of claim 2, wherein the molar ratio of 5-carbamoyl-4-lower alkyl-oxazole:cyanuric chloride in the reaction is from about 3:1 to about 3:10, and the molar ratio of the N,N-disubstituted formamide:cyanuric chloride is at least 3:1.

4. The process of claim 3, wherein the molar ratio of 5-carbamoyl-4-lower alkyl-oxazole:cyanuric chloride is from about 3:1 to about 1:1.

5. The process of claim 4, wherein the molar ratio of 5-carbamoyl-4-lower alkyl-oxazole:cyanuric chloride is about 2:1.

6. The process of claim 3, wherein the N,N-disubstituted formamide is N,N-dimethylformamide and the 5-carbamoyl-4-lower alkyl-oxazole is 5-carbamoyl-4-methyl-oxazole.

* * * * *